(12) United States Patent
Sadritabrizi

(10) Patent No.: US 6,471,657 B2
(45) Date of Patent: Oct. 29, 2002

(54) USER RELEASABLE AND ADJUSTABLE BLOOD PRESSURE CUFF AND METHOD

(75) Inventor: Alireza Sadritabrizi, Issaquah, WA (US)

(73) Assignee: Spacelabs Medical, Inc., Redmond, WA (US)

( * ) Notice: Subject to any disclaimer, the term of this patent is extended or adjusted under 35 U.S.C. 154(b) by 0 days.

(21) Appl. No.: 09/775,314

(22) Filed: Jan. 31, 2001

(65) Prior Publication Data

US 2002/0103440 A1 Aug. 1, 2002

(51) Int. Cl.[7] .................................................. A61B 5/02
(52) U.S. Cl. ........................ 600/499; 600/485; 600/490; 600/491
(58) Field of Search ................................ 600/485, 488, 600/490–496, 448, 499; 128/900; D24/165

(56) References Cited

U.S. PATENT DOCUMENTS

| | | | |
|---|---|---|---|
| 3,935,984 A | | 2/1976 | Lichowsky et al. ......... 600/499 |
| 4,109,646 A | | 8/1978 | Keller |
| 4,116,230 A | | 9/1978 | Gorelick |
| 4,206,765 A | | 6/1980 | Huber |
| 4,300,573 A | * | 11/1981 | Rebbe et al. ................ 600/499 |
| 4,353,374 A | | 10/1982 | Rebbe et al. |
| 4,549,550 A | * | 10/1985 | Kami ........................... 600/499 |
| D290,876 S | * | 7/1987 | Arduini et al. ............. D24/165 |
| 4,716,906 A | | 1/1988 | Ruff |
| 4,727,885 A | | 3/1988 | Ruff |
| 4,745,924 A | | 5/1988 | Ruff |
| 4,832,040 A | | 5/1989 | Ruff |
| 4,838,276 A | | 6/1989 | Nagai et al. |
| 4,844,306 A | | 7/1989 | Ruff et al. ................... 224/600 |
| 4,890,625 A | | 1/1990 | Sorensen |
| 5,069,219 A | | 12/1991 | Knoblich |
| 5,188,115 A | * | 2/1993 | Otani .......................... 600/490 |
| 5,277,187 A | | 1/1994 | Pillsbury |
| 5,421,341 A | * | 6/1995 | Marangoni ................. 600/490 |
| 5,467,772 A | * | 11/1995 | Souma ........................ 600/493 |
| D371,844 S | | 7/1996 | Sadritabrizi et al. ........ D24/165 |
| 5,595,180 A | * | 1/1997 | Ogura et al. ................ 600/499 |
| 5,620,001 A | | 4/1997 | Byrd et al. |
| 6,213,953 B1 | * | 4/2001 | Reeves ........................ 600/499 |

* cited by examiner

Primary Examiner—Kevin Shaver
Assistant Examiner—Patricia Mallari
(74) Attorney, Agent, or Firm—Dorsey & Whitney LLP

(57) ABSTRACT

The present invention is directed to a method and apparatus for obtaining blood pressure measurements employing a user releasable and adjustable blood pressure cuff. In one aspect of the invention, the blood pressure cuff apparatus consists of a first cuff member connected to a mounting surface and rotatable about a first axis of rotation substantially perpendicular to the mounting surface. The first cuff member is connected to a second cuff member that is rotatable about a second axis of rotation that is substantially perpendicular to the first. A blood pressure cuff comprised of a loop adapted to receive the arm of a test subject is connected to the second cuff member. In another aspect of the invention, the elongated flexible band has a first end and a second end. The first end is connected to the second member of the cuff housing, and the second end is connected to a cuff retainer. The cuff retainer is releasibly latchable from the second member so that the elongated flexible band forms a loop to snugly fit the arm of the test subject with a first circumferential length when the cuff retainer is latched. When the cuff retainer is unlatched, the elongated flexible band forms a loop with a second circumferential length, which allows the arm of the test subject to be easily withdrawn.

52 Claims, 4 Drawing Sheets

USER RELEASABLE AND ADJUSTABLE BLOOD PRESSURE CUFF AND METHOD

TECHNICAL FIELD

This invention relates to blood pressure measurements, and more particularly to a blood pressure cuff that may be easily installed around the arm and released.

BACKGROUND OF THE INVENTION

Hypertension in adults is regarded as a significant health risk since the symptoms of the disease are not apparent to the individual. The presence of the disease in the individual may therefore remain hidden until a catastrophic health event, such as a heart attack, or a stroke occurs. Fortunately, initial diagnosis of the condition is easily accomplished by a simple blood pressure measurement. Consequently, automatic blood pressure monitoring stations have become widely available to the general public that allow blood pressure measurements to be self-administered. An example of one such system is the VITA-STAT™ blood pressure monitoring station manufactured by Spacelabs Medical, Inc. of Redmond, Washington, which is shown in U.S. Pat. No. D-371,844 to Sadritabrizi, et al. Briefly, the VITA-STAT™ station consists of a kiosk, in which a test subject can be accommodated in a sitting position. The test subject then places an upper arm into a blood pressure cuff apparatus that constricts the flow of blood in an artery to obtain blood pressure measurements at systole and diastole. A processor accepts and processes blood pressure signals obtained from the cuff apparatus during the examination, and subsequently displays the processed information to the test subject on a monitoring device.

A significant difficulty encountered in self-administered blood pressure measurements is the application of the blood pressure cuff to the test subject. The flat, flexible cuff commonly associated with the sphygmomanometer is particularly unsuited for use in automatic blood pressure monitoring stations, since the application of the flexible cuff around the arm of the test subject is difficult to accomplish without assistance. Moreover, once properly positioned, it must be secured into place by hooks, elastic bands, or specialized fasteners such as VELCRO™. As a consequence, a number of automatic cuff devices have been developed for use with automatic blood pressure monitoring stations. An example of a self-installing cuff apparatus is described in U.S. Pat. No. 4,109,646 to Keller, which uses a motor-driven rotating drum to continuously wrap a blood pressure band onto a limb of a test subject that is placed within the drum. Removal of the blood pressure band from the test subject is accomplished by reversing the motor. A similar technique is described in U.S. Pat. No. 4,206,765 to Huber, which uses a motor driven tensioning drum to tension the blood pressure band around the limb of a test subject. A slip clutch is provided to prevent over tensioning of the blood pressure band during the application of the band to the test subject. U.S. Pat. No. 3,935,984 to Lichowsky, et al., uses a mechanical cable wrapped around the blood pressure band to snug the band tightly about the arm of the test subject. Release of the test subject's arm is similarly accomplished by reversing the direction of the motor.

A significant shortcoming of these prior art devices is that they rely on a blood pressure band tensioning means that requires a blood pressure band tensioning drive motor and mechanism, which adds to the cost and complexity of the blood pressure monitoring station. Further, since the tensioning means is motor driven, some means must be provided to allow the test subject to release the blood pressure cuff in the event of a power failure, or to protect the test subject from over-tensioning the band due to system malfunctions. The release mechanisms employed in prior art devices have not, in general, adequately addressed these abnormal operating conditions. Additionally, a particular shortcoming present in the prior art devices is that there is no provision for a release mechanism that allows the band tension and the pneumatic pressure in the band to be released simultaneously through a user actuated release.

The self-installing cuff used with the VITA-STAT™ blood pressure monitoring station mentioned previously does not rely on a motor driven tensioning means to snug the blood pressure band about the arm. Instead, the arm is tightly confined within a fixedly mounted cylindrical housing that retains the inflatable blood pressure band. The use of a cylindrical, non-resilient member to retain the inflatable band also has some drawbacks. A limit on the maximum cylinder diameter exists because the blood pressure band must achieve adequate snugness prior to inflation. Since the cylinder diameter is generally sized according to median estimates of upper arm diameter, some individuals may find that the cylindrical cuff apparatus simply cannot accommodate them. In other cases, some individuals may damage the flexible blood pressure band inside the cylinder by unsuccessfully attempting to insert their upper arms into the cylinder, which may render the blood pressure cuff apparatus unusable, or cause it to yield inaccurate measurements. Still other individuals may misalign the upper arm with the cylindrical housing so that a successful inflation of the blood pressure band is impeded, resulting in an erroneous blood pressure reading. Finally, some individuals may find the insertion of the arm into a closed cylindrical member that subjects the arm to a constriction too psychologically intimidating to use.

A further drawback present in all prior art cuff devices is that they lack an ergonomic adjustment feature. Typically, automatic blood pressure devices, such as the VITA-STAT™ blood pressure monitoring station, accommodate the test subject in a seated position while undergoing a blood pressure test. Since the orientation of the cuff assembly cannot be adjusted, the test subject must make suitable adjustments in body position to properly align the arm in the cuff assembly prior to inflation of the internal band, and maintain the arm in the aligned position until the blood pressure evaluation is complete. As a consequence, individuals whose bodily dimensions significantly differ from median estimates cannot be accommodated by the blood pressure cuff in a comfortable manner.

Accordingly, there is a need in the art for a cuff assembly that does not use a motor driven band tensioning devices to tension the band prior to inflation, and that provides a cuff release capability to a greater degree than present in prior art devices. Further, there is also a need in the art for a cuff apparatus that does not rely on a confining cylindrical member to retain the inflatable band. Finally, the cuff assembly should provide an ergonomic adjustment capability that will permit the proper alignment of the blood pressure cuff with the arm to be conveniently attained during a blood pressure measurement, which, at the same time, enhances the comfort of the test subject.

Other advantages of the invention will become apparent based upon the description of the invention provided below when read with reference to the drawing figures.

SUMMARY OF THE INVENTION

The present invention is directed to a method and apparatus for obtaining blood pressure measurements employing a user releasable and adjustable blood pressure cuff. In one aspect of the invention, the blood pressure cuff apparatus consists of a first cuff member connected to a mounting surface and rotatable about a first axis of rotation substantially perpendicular to the mounting surface. The first cuff member is connected to a second cuff member that is rotatable about a second axis of rotation that is substantially perpendicular to the first. A blood pressure cuff comprised of a loop adapted to receive the arm of a test subject is connected to the second cuff member. In another aspect of the invention, the elongated flexible band has a first end and a second end. The first end is connected to the second member of the cuff housing, and the second end is connected to a cuff retainer. The cuff retainer is releasibly latchable from the second member so that the elongated flexible band forms a loop to snugly fit the arm of the test subject with a first circumferential length when the cuff retainer is latched. When the cuff retainer is unlatched, the elongated flexible band forms a loop with a second circumferential length, which allows the arm of the test subject to be easily withdrawn.

Figure 1:
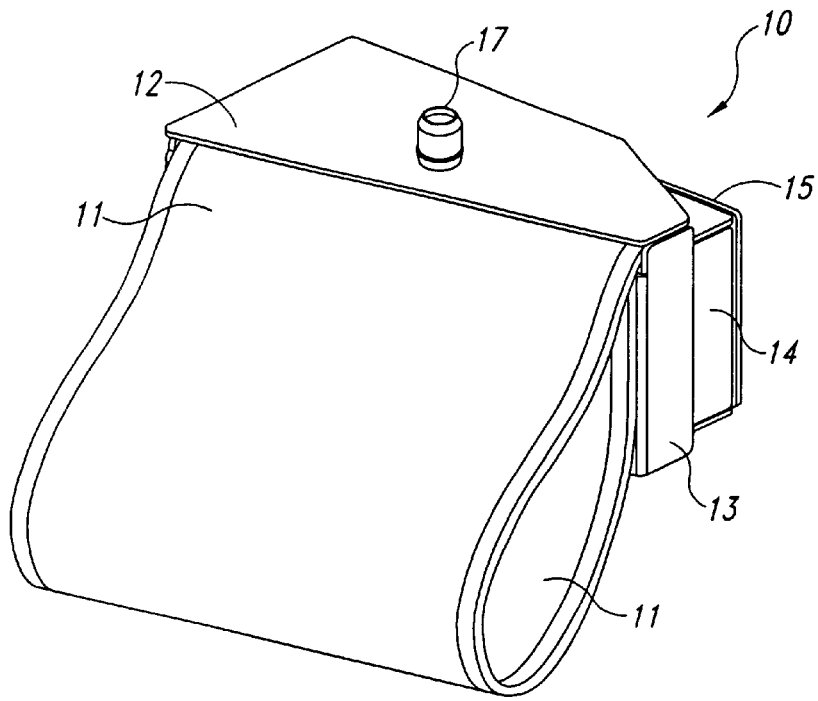
FIG. 1 is a frontal isometric view of one embodiment of the user releasable and adjustable automatic cuff apparatus.

In the drawings, like reference numbers identify similar elements or steps. For ease in identifying the discussion of any particular element, the most significant digit in a reference number refers to the Figure number in which the element is first introduced (e.g., element 24 is first introduced and discussed with respect to FIG. 2).

DETAILED DESCRIPTION OF THE INVENTION

For purposes of the following description, the terms "upper", "lower", "front" and "back" and relative terms of similar reference shall refer to the orientation of the invention a shown in FIGS. 1 through 7, except where expressly specified to the contrary. Specific dimensions and other physical characteristics related to different embodiments are not to be considered as limiting unless the claims expressly state otherwise.

FIG. 1 illustrates an embodiment of the user releasable and adjustable blood pressure cuff according to the invention. The blood pressure cuff 10 includes an elongated flexible band 11 with inner and outer surface layers. The band 11 also has a plurality of air-impermeable compartments (not shown) between the inner and outer surface layers that can be connected to a pressurization source to allow the band 11 to be inflated prior to a blood pressure measurement. The elongated flexible band 11 is preferably formed of layers of a durable woven fabric such as nylon, and the air impermeable compartments located between the inner and outer layers are preferably retained in position by stitching. Alternatively, other structures could be used to form the band 11, such as fabricating the band 11 from rubber-impregnated fabrics, or from entirely non-woven resilient materials such as elastomers. The band 11 may also be fabricated as a single structure, with the air impermeable compartments formed within the band.

Still referring to FIG. 1, the blood pressure cuff 10 further includes an outer housing 13, and an inner housing 14 that are rotationally connected to allow ergonomic adjustment to the test subject. A swivel plate 15, which is rotationally connected to the inner housing 14, provides additional rotational flexibility. The rotational relationship between the outer cuff housing 13, the inner cuff housing 14 and the swivel plate 15 will subsequently be described in greater detail in connection with other figures. The outer cuff housing 13 is a box like structure having top and bottom sides, and having a back side, which is preferably open. The back side of the outer cuff housing 13 is adapted to receive an inner cuff housing 14, so that inner cuff housing 14 can be at least partially recessed within the outer cuff housing 13. The inner cuff housing 14 is similarly a boxlike structure with top and bottom sides, an open front side (not shown) and a back side. When inner cuff housing 14 is recessed within outer cuff housing 13, an enclosure is formed which contains internal elements of the apparatus, that will be discussed more fully in connection with a subsequent figure.

Figure 2:
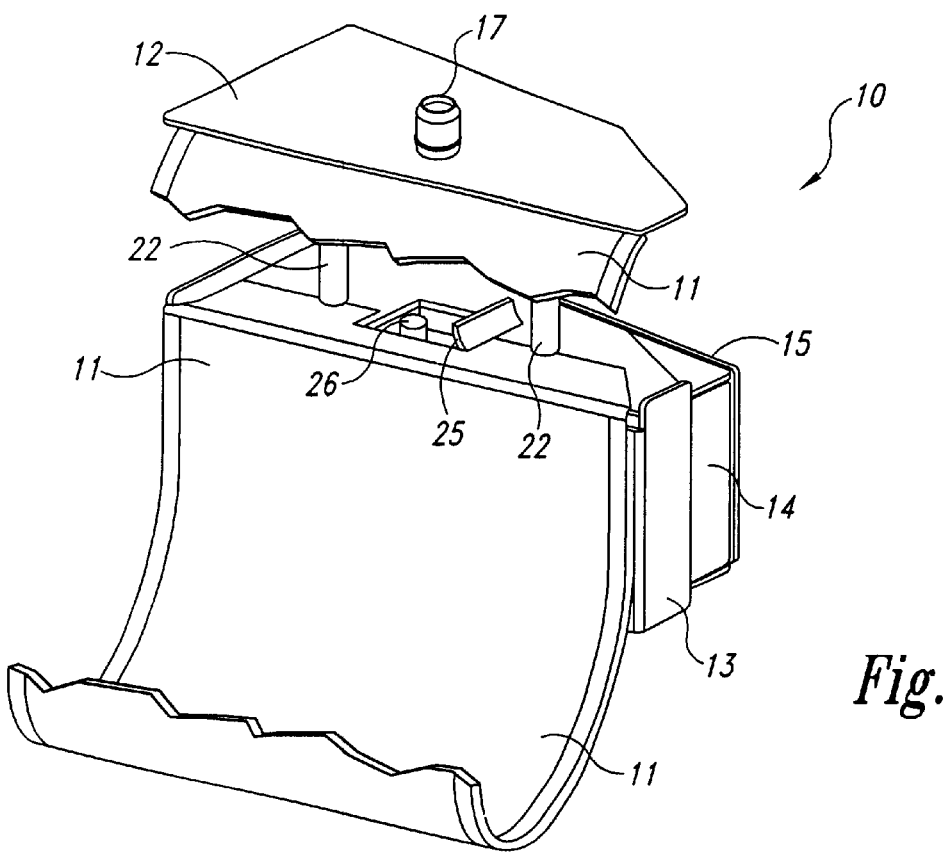
FIG. 2 is a frontal isometric view the embodiment of the user releasable and adjustable automatic cuff apparatus shown in FIG. 1 with the release mechanism shown in the open position.
Figure 4:
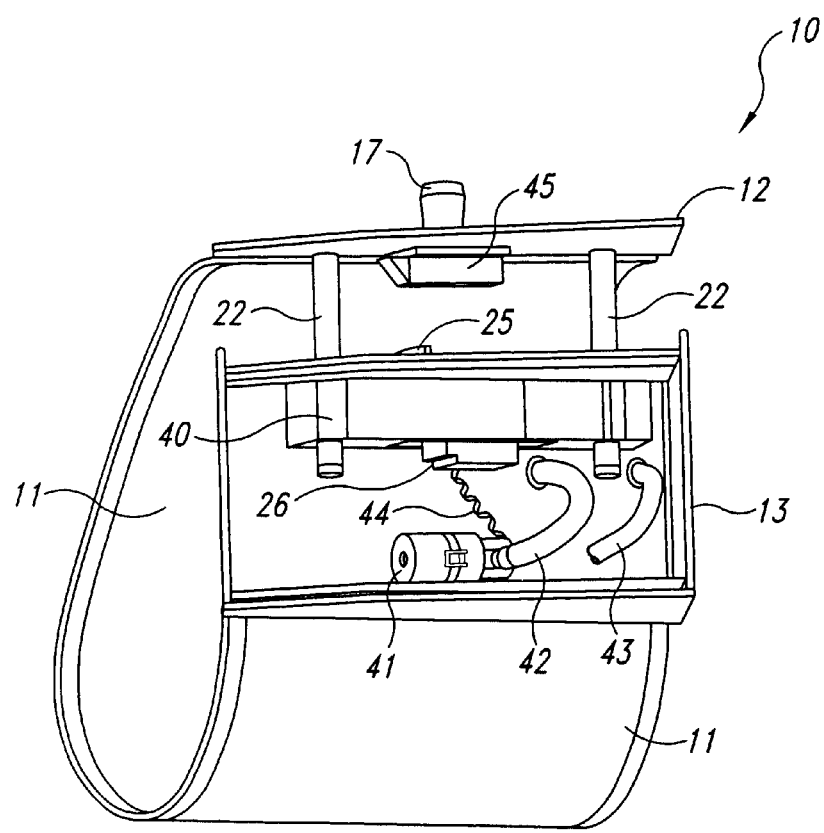
FIG. 4 is a rear isometric view the embodiment of the user releasable and adjustable automatic cuff apparatus shown in FIG. 1 with the release mechanism shown in the open position and the inner housing removed to show internal details.

With reference now to FIG. 2, a first end of the band 11 is attached to the outer cuff housing 13 by metal retainer strips 23 which are held in place by screws. The other end of the band 11 is similarly attached by metal retainer strips 46 (as best seen in FIG. 4) to the cuff retainer 12, to form the loop 19. Although the retainer strips 23 and 46 securely hold the ends of the band to the outer cuff housing 13 and the cuff retainer 12 by clamping means, other means for attaching the band 11 to the outer cuff housing 13 and to the cuff retainer 12 are possible.

Still referring to FIGS. 1 and 2, the cuff retainer 12 is located on the top side of the outer cuff housing 13 and is held in a position adjoining outer housing 13 by a latching mechanism (not shown). When the cuff retainer 12 is latched to the top side of the outer cuff housing 13, the loop 19 has a minimum circumferential length so that the band 11 forms a snug fit about the arm of the test subject. As shown in FIG. 2, where the elongated flexible band 11 has been partially cut away, the cuff retainer 12 is free to translate away from the top of the outer cuff housing 13 when the cuff retainer 12 is released. As a result, the circumferential length of the loop 19 increases when the cuff retainer 12 is in the released state, which allows the test subject additional freedom of movement during withdrawal of the limb.

Referring now to FIGS. 2 and 4, where the cuff retainer 12 is shown in the unlatched state, the cuff retainer is supported by a pair of support rods 22 securely attached to the under side of cuff retainer 12. The support rods 22 slide through access holes 27 and through linear bearings 40 to restrict the cuff retainer 12 to vertical movement relative to the outer cuff housing 13. The cuff retainer 12 further includes a release knob 17, which allows manual release of the cuff retainer 12 from a latched condition when actuated. The release mechanism will be described in more detail in connection with subsequent figures.

Although the support rods 22 as shown in FIG. 2 are securely attached to the cuff retainer 12, other support rod configurations are possible. For example, the cuff retainer 12 may be supported by a single support rod, which has a longitudinal surface groove that engages a key in the outer cuff housing 13 to prevent rotation of the cuff retainer 12 relative to the outer cuff housing 13 when the cuff retainer 12 is released. Alternatively, more than two support rods may also be used. Still another configuration may be obtained when the support rods are securely attached to the outer cuff housing, with the cuff retainer 12 sliding along the stationary support rods when the cuff retainer is released.

Figure 3:
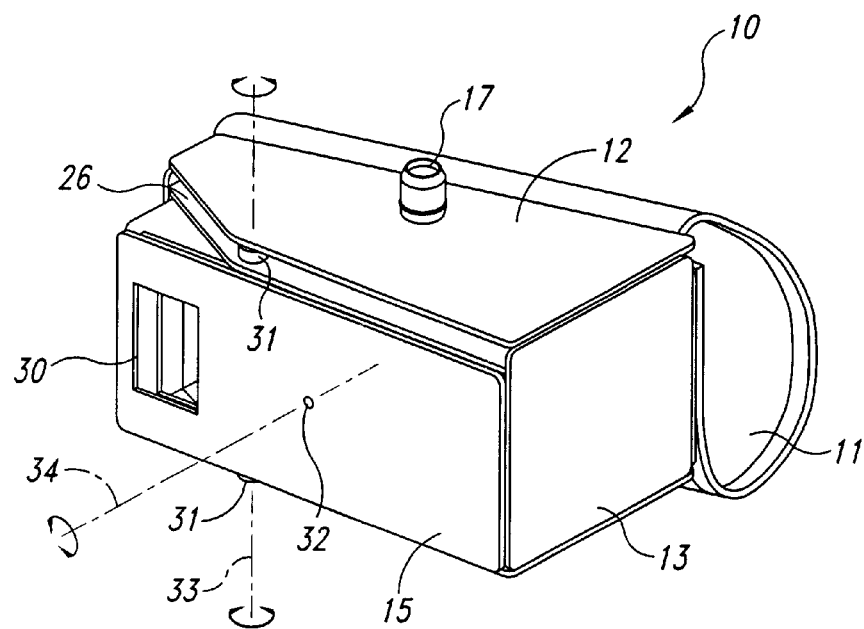
FIG. 3 is a rear isometric view the embodiment of the user releasable and adjustable automatic cuff apparatus shown in FIG. 1.

Turning now to FIG. 3, the rotational relationship between the outer cuff housing 13 and the inner cuff housing 14 and the swivel plate 15 will now be discussed. With the inner cuff housing 14 recessed into the outer cuff housing 13, the inner cuff housing 14 and the outer cuff housing 13 are preferably connected by a pair of pivot screws 31 which are inserted through the top and bottom sides of the outer cuff housing 13 to engage threads in adjacent holes in the inner cuff housing 14. Rotational movement between the outer cuff housing 13 and inner cuff housing 14 about an axis 33 that projects through the centerline of the pivot screws 31 is thus attained. Since the rotational axis 33 is shown at an intermediate position along the length of the outer cuff housing 13, a clearance bevel 35 is formed in the outer cuff housing 13 to permit rotation of the outer cuff housing 13 about the axis 33. The back side of the inner cuff housing 14 is connected to swivel base 15 by a screw 32 (not shown). The swivel plate 15 is a thin, flat member with attachment holes 35 to permit secure attachment to a fixed support. An access hole 30 is provided in the swivel base 15 to allow routing of electrical wiring and pneumatic tubing from an external monitoring device (not shown) into the interior of the enclosure formed by the outer cuff housing 13 and inner cuff housing 14. The screw 32 permits rotational movement of the inner cuff housing 14 relative to the swivel plate 15 about an axis 34, which is substantially perpendicular to the axis 33. Accordingly, rotational motion of the blood pressure cuff 10 about the mutually perpendicular axes 33 and 34 provides the blood pressure cuff 10 with an ergonomic adjustment feature that allows the blood pressure cuff 10 to be conveniently adjusted to the test subject's body position when the upper arm of the test subject is inserted into the loop 19.

Although the present embodiment preferably uses pivot screws 31 and a swivel plate 15 to attain rotational movement about the mutually perpendicular axes 33 and 34, other equally feasible means are available for establishing these rotational relationships. For example, a hinge pin could be substituted for the pivot screws 31 to allow rotation of the outer cuff housing 13 about axis 33. Rotation of the inner cuff housing about axis 34 may also be obtained when the screw 32 is also used to in mount the blood pressure cuff 10 to a fixed support, thus eliminating the swivel plate 15.

Internal components of the blood pressure apparatus 10 will now be described with reference to FIG. 4. In order to view these internal components, FIG. 4 shows the blood pressure apparatus 10 with the inner cuff housing 14 and swivel plate 15 removed, and also shows the cuff retainer 12 in the unlatched state for clarity. FIG. 4 shows pneumatic pressure relief components located within the blood pressure cuff 10 which allow pressurized air contained within the band 11 to be exhausted to the surroundings when the cuff retainer 12 is moved from the latched state to the released state. An electrical switch 26, located within the housing 39 is connected by a wire 44 to an electrically actuated valve 41, which is, in turn, connected to a source of electrical energy through wire 46. When the cuff retainer 12 is moved from the latched state to the released state, the electrical switch 26 located in the housing 39 is moved to a relaxed state, which causes the electrically actuated valve 41 to open. Pressurized air held within the band 11 is thus released from the band 11 through the flexible tube 42, where it is exhausted to the surroundings through the valve 41. Actuation of the switch 26 may additionally be used to provide an indication to the monitoring station that the band 11 is snug about the arm of the test subject, and flexible band is ready to be inflated.

Alternative approaches may be used to release pressurized air within the band 11 when the cuff retainer 12 is unlatched. For example, a mechanical valve which is opened by a mechanical linkage attached to cuff retainer 12 may be substituted for the electrical components described above, thus eliminating the need for a source of electrical energy. Further, where electrical components are used, alternative circuit designs are possible. For example, the electrical switch 26 may be of the normally closed, or normally open type. Similarly, the electrically actuated valve 41 may be in the open state when electrical energy is applied, or when it is removed, depending on the configuration of the electric circuit.

Still referring to FIG. 4, the latching mechanism will now be described. Attached to cuff retainer 12 is a latching mechanism 45 with a spring-loaded pawl 47. When the cuff retainer 12 is moved to the latched position (as shown in FIG. 1), the pawl 47 engages an aperture 25 to latch the cuff retainer 12 securely to the outer cuff housing 13. When the pawl 47 is engaged with the aperture 25, the latching mechanism 45 is concealed within a recess 24 (best seen in FIG. 2) in the linear bearing assembly 40. When the latching mechanism 45 is concealed in the recess 24, the latching mechanism 45 also engages and actuates the electrical switch 26.

Alternatives to the mechanical latching mechanism 45 are available, and may be substituted for the mechanical device shown. For example, an electrically actuated latching device, such as a spring-loaded solenoid latch, may replace the mechanical latching mechanism 45. Still other means, such as pneumatic latching mechanisms, may also be used.

Figure 5A:
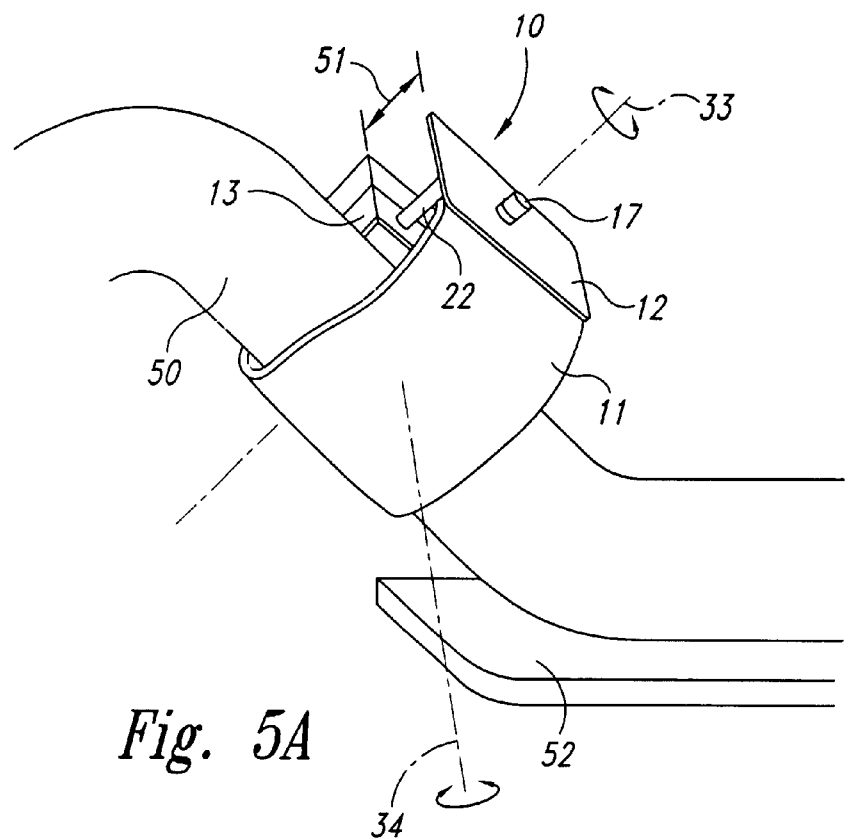
FIG. 5 is an isometric view of the embodiment of the user releasable and adjustable automatic cuff apparatus in FIG. 1 shown receiving an upper arm for a blood pressure determination.
Figure 5B:
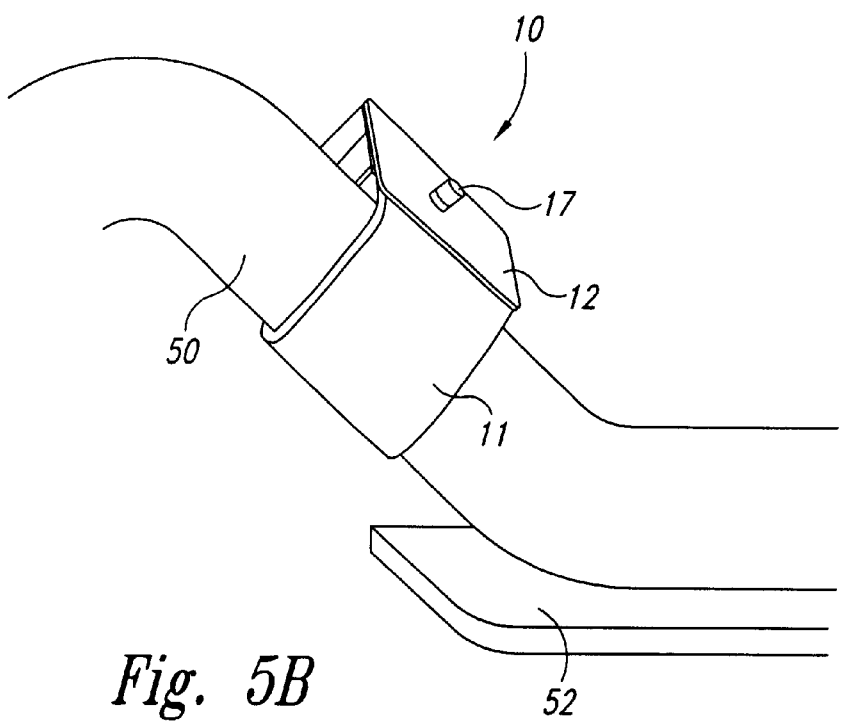

FIGS. 5(a) and (b) illustrate the operation of the blood pressure cuff 10 during a blood pressure measurement. As shown in FIG. 5(a), an upper arm 50 of a test subject is inserted into the circumferential loop formed by the band 11, while the remainder of the arm rests on a supporting surface 52. The cuff retainer 12 is also shown in the released state, with the support rods 22 fully extended from the outer cuff housing 13. When the cuff retainer 12 is in the released state, the circumferential length of the loop 19 formed by the band 11 is increased by approximately a length 51, which affords the test subject additional freedom of movement within the loop 19. In preparation for the blood pressure determination, the test subject may adjust the orientation of the band 11 through manual manipulations about the two independent axes of rotation 33 and 34 to accommodate his body position. Before a measurement can be made, the cuff retainer 12 must be moved to the latched condition, as shown in FIG. 5(b). At this point, the band 11 is held snugly about the upper arm 50, and the electrical switch 26 (not shown in FIG. 5) has been actuated by the latching mechanism 45 (also not shown in FIG. 5) causing the electrically actuated valve 41 to close. Upon commencement of the blood pressure measurement, the band 11 is inflated by a pneumatic source, which causes constriction of the blood flow in an artery within the upper arm 50. When the flow is fully constricted, air is bled from the band 11 at a controlled rate, whereupon systolic and diastolic determinations are made by conventional means. At the conclusion of the measurement, the test subject actuates the release knob 17 to allow the cuff retainer 12 to move to the released state. Since the electrical switch 26 is moved to the deactivated state when the cuff retainer 12 is released, the electrical switch 26 causes the electrically actuated valve 41 (not shown in FIG. 5) to depressurize the band 11. If it is desired to terminate the blood pressure evaluation prior to completion, the test subject may actuate the release knob 17 at any time to simultaneously release the cuff retainer 12 and depressurize the band 11.

Figure 6:
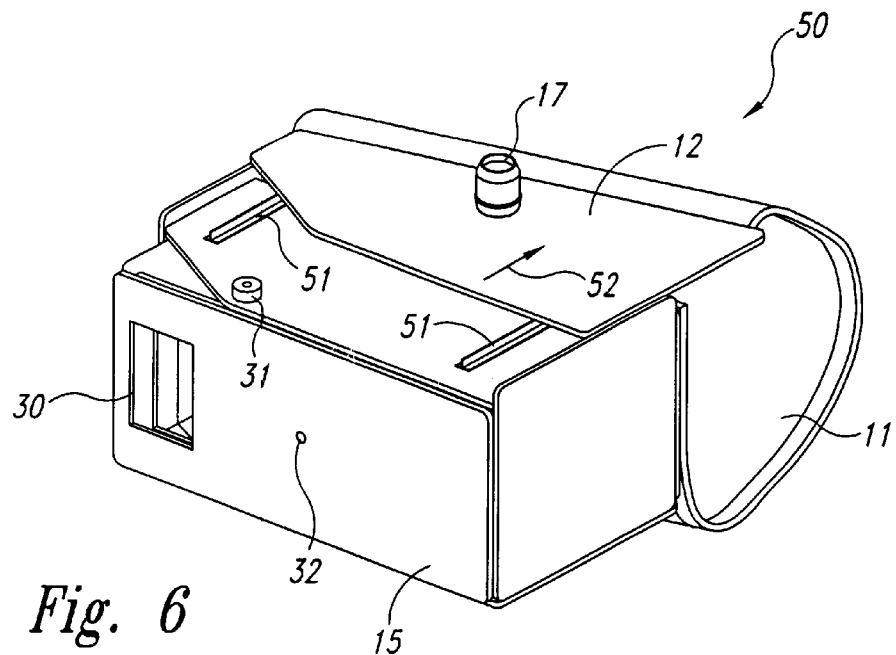
FIG. 6 is a rear isometric view of an alternative embodiment of the user releasable and adjustable automatic cuff apparatus.

FIG. 6 illustrates an alternative embodiment of the invention. In this embodiment, the cuff retainer 12 is allowed to translate along guide surfaces 51 in a direction 52 when cuff retainer 12 is in the released state in order to permit the test subject to remove his arm. The released state affords the test subject additional freedom of movement by increasing the circumferential length of the loop by a length 53. As in the previous embodiment, release of the cuff retainer 12 will simultaneously deactivate an electrical switch (not shown in FIG. 6), or other similar means, to depressurize the band 11.

Figure 7:
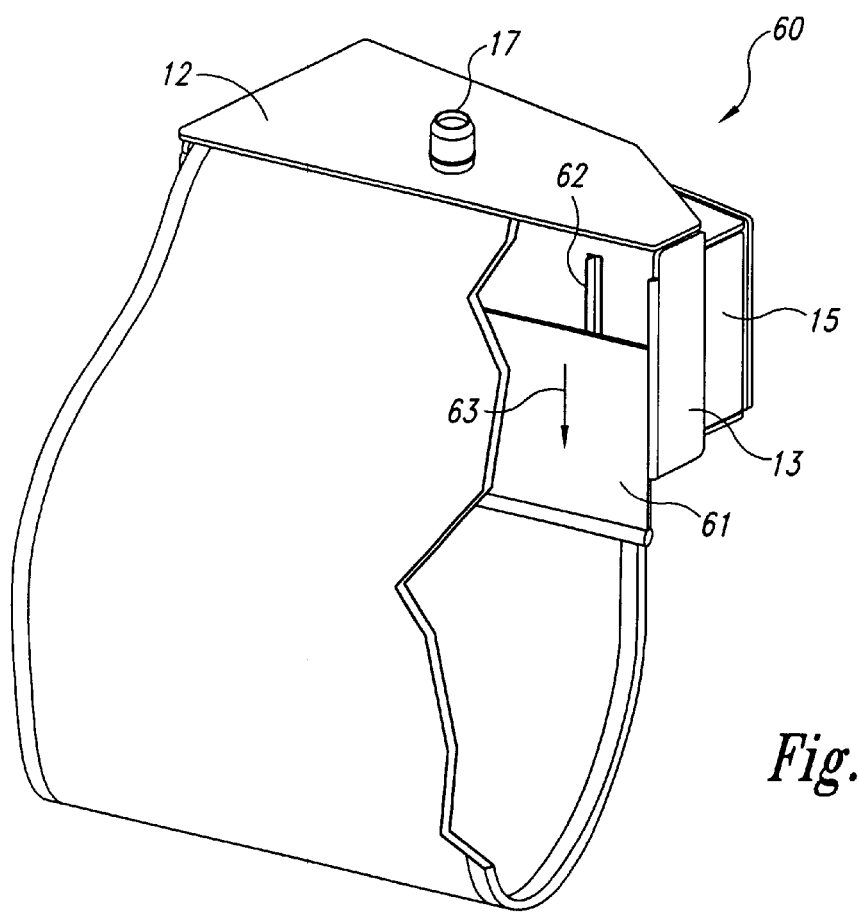
FIG. 7 is a frontal isometric view of an alternative embodiment of the user releasable and adjustable automatic cuff apparatus.

FIG. 7 illustrates still another alternative embodiment of the invention. In this embodiment, the cuff retainer 12 coincides with the top surface of outer cuff housing 13. Actuation of release knob 17 allows a slidable member 71 to translate along guide surfaces 72 in a direction 73 in order to increase the circumferential length of the loop by a length 74. As in the previous embodiments, actuation of the release knob 17 will simultaneously deactivate an electrical switch (not shown in FIG. 7), or other similar means, to depressurize the band 11.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope the invention, as those skilled in the relevant art will recognize. Moreover, the various embodiments described above can be combined to provide further embodiments. Accordingly, the invention is not limited by the disclosure, but instead the scope of the invention is to be determined entirely by the following claims.

What is claimed is:

1. A pneumatic blood pressure cuff apparatus for blood pressure measurements, comprising:
    a first cuff member rotatably connected to a mounting surface and rotatable about a first axis of rotation substantially perpendicular to the mounting surface;
    a second cuff member rotatably connected to the first member and rotatable about a second axis of rotation substantially perpendicular to the first axis; and
    an elongated inflatable flexible band of predetermined length forming a loop connected to the second cuff member, the loop being adapted to receive a limb.

2. The apparatus of claim 1 wherein said first member is further comprised of a swivel plate adapted to be attached to a support surface.

3. The apparatus of claim 2 wherein the first cuff member is further comprised of an inner cuff housing with a front side adapted to attach the loop, and the second cuff member is further comprised of an outer cuff housing with back side adapted to attach the swivel plate, the inner cuff housing being adapted to be at least partially recessed within the outer cuff housing to form an enclosure.

4. The apparatus of claim 3 wherein the inner cuff housing and outer cuff housing are further comprised of a top and a bottom side, the outer cuff housing being rotatively coupled to the inner cuff housing by a first pivot screw projecting from the top side of the inner cuff housing through the top side of the outer cuff housing, and a second pivot screw projecting from the bottom side of the inner cuff housing through the bottom side of the outer cuff housing.

5. The apparatus of claim 1 wherein said first member and said second member are rotatably connected using a hinge.

6. The apparatus of claim 1 wherein said elongated flexible band is comprised of an air-impermeable fabric.

7. The apparatus of claim 1 wherein said elongated flexible band is comprised of an air-impermeable elastomer.

8. A pneumatic blood pressure cuff apparatus for blood pressure measurements, comprising:
- an elongated flexible band of predetermined length adapted to be inflated, the length having a first and a second end;
- a cuff housing attached to a first end of the elongated flexible band; and
- a cuff retainer connected to the second end of the elongated flexible band, the cuff retainer including a latching mechanism, and the cuff housing including a receiver adapted to latchably engage the latching mechanism, the latching mechanism having an actuator connected to the latching mechanism to releasably latch the cuff housing, and wherein the elongated flexible band forms a loop with a first circumferential length when the cuff retainer is in a latched state, and the elongated flexible band forms a loop with a second circumferential length when in the unlatched state, the second circumferential length being greater than the first circumferential length.

9. The apparatus of claim 8 wherein the latching mechanism is further comprised of a pawl, and the receiver is an aperture adapted to latchably engage the pawl.

10. The apparatus of claim 8 wherein the actuator is further comprised of a manual release knob accessible to the user.

11. The apparatus of claim 8 wherein the latching mechanism is further comprised of an electrically actuated solenoid.

12. The apparatus of claim 8 wherein the latching mechanism is further comprised of a pneumatically actuated air cylinder.

13. A pneumatic blood pressure cuff apparatus for blood pressure measurements, comprising:
- an elongated flexible band of predetermined length adapted to be inflated, the length having a first and a second end;
- a cuff housing attached to a first end of the elongated flexible band; and
- a cuff retainer connected to the second end of the elongated flexible band, the cuff retainer being releasably latchable and slidably connected to the cuff housing, wherein the elongated flexible band forms a loop with a first circumferential length when the cuff retainer is in a latched state, and the elongated flexible band forms a loop with a second circumferential length when in the unlatched state, the second circumferential length being greater than the first circumferential length, and further wherein the cuff retainer and the cuff housing are slidably connected by at least one linear guide track adapted to permit translation of the cuff retainer relative to the cuff housing when the cuff retainer is in the unlatched state.

14. The apparatus of claim 8 wherein the cuff housing is further comprised of a top surface with at least one support rod attached to the top surface and projecting away from the cuff housing in a substantially perpendicular direction, and the cuff retainer is further comprised of a bottom surface with at least one linear bearing adapted to receive the at least one support rod, wherein the at least one support rod and the at least one linear bearing form a slidable connection permitting the cuff retainer to translate away from the cuff housing when the cuff retainer is in the unlatched state.

15. The apparatus of claim 8 wherein the cuff retainer is further comprised of a latching mechanism having an actuator connected to the latching mechanism and the cuff housing is further comprised of a receiver adapted to latchably engage the latching mechanism when the cuff retainer is in the latched position.

16. The apparatus of claim 15 wherein the latching mechanism is further comprised of a pawl, and the receiver is an aperture adapted to latchably engage the pawl.

17. The apparatus of claim 15 wherein the actuator is further comprised of a manual release knob accessible to the user.

18. The apparatus of claim 15 wherein the latching mechanism is further comprised of an electrically actuated solenoid.

19. The apparatus of claim 15 wherein the latching mechanism is further comprised of a pneumatically actuated air cylinder.

20. The apparatus of claim 13 wherein the cuff housing is further comprised of a top surface, and the at least one linear guide track is attached to the top surface of the cuff housing and adapted to permit translation of the cuff retainer relative to the top surface of the cuff housing when the cuff retainer is in the unlatched state.

21. The apparatus of claim 13 wherein the cuff housing is further comprised of a front surface, and the at least one linear guide track is attached to the front surface of the cuff housing and adapted to permit translation of the cuff retainer relative to the front surface of the cuff housing when the cuff retainer is in the unlatched state.

22. The apparatus of claim 13 wherein the cuff retainer is further comprised of a bottom surface with at least one support rod attached to the bottom surface and projecting away from the cuff retainer in a substantially perpendicular direction, and the cuff housing is further comprised of a top surface with at least one linear bearing adapted to receive the at least one support rod, wherein the at least one support rod and the at least one linear bearing form a slidable connection permitting the cuff retainer to translate away from the cuff housing when the cuff retainer is in the unlatched state.

23. A pneumatic blood pressure cuff apparatus for blood pressure measurements, comprising:
- an elongated flexible band of predetermined width and length, the length having a first and a second end, the elongated flexible band having at least one air impermeable compartment adapted to be inflated;
- a cuff housing with a first side and a second side, the first side being rotatably mounted to a mounting surface and capable of a first rotation about a first axis of rotation substantially perpendicular to the mounting surface, and a second side which is hingeably connected to the first side and capable of a second rotation about a second axis of rotation substantially perpendicular to said first axis, wherein the first and second rotations allow the apparatus to be ergonomically adjusted to a limb of a test subject;
- a cuff retainer releasably connected to the second side of the cuff housing and having a latched state and a released state, the cuff retainer being attached to the second end of the elongated flexible band to form a loop with a first circumferential length for snugly receiving a limb when the cuff retainer is in the latched state and forming a loop with a second circumferential length which is larger than the first when the cuff retainer is in the released state; and a cuff release connected to the cuff retainer to select the latched state and the released state.

24. The apparatus of claim 23 wherein the first side is further comprised of an inner cuff housing and the second side is further comprised of an outer cuff housing, the inner cuff housing being at least partially recessible within the outer cuff housing, wherein the inner cuff housing and the outer cuff housing are pivotally connected to form the second axis of rotation.

25. The apparatus of claim 24 wherein the cuff retainer is further comprised of a bottom side having at least one support rod projecting substantially perpendicular therefrom, and the outer cuff housing has at least one linear bearing adapted to receive the at least one support rod, the support rod and the linear bearing thus allowing the the cuff retainer to move away from the outer cuff housing when the cuff retainer is in the released state.

26. The apparatus of claim 24 wherein the inner cuff housing is further comprised of a swivel plate that forms the first axis of rotation, which is further adapted to be mounted to a fixed surface.

27. The apparatus of claim 23 wherein said cuff release is further comprised of a latching mechanism with a pawl on said second member adapted to latchably engage a member on said cuff retainer adapted to receive said pawl.

28. The apparatus of claim 23 wherein the cuff release is further comprised of a latching mechanism with a pawl adapted to latchably engage an aperture on the second member adapted to receive the pawl.

29. A pneumatic blood pressure cuff apparatus for blood pressure measurements, comprising:

an elongated flexible band of predetermined length adapted to be inflated, the length having a first and a second end;

a cuff housing attached to a first end of the elongated flexible band; and a cuff retainer connected to the second end of the elongated flexible band, the cuff retainer being releasably latchable to the cuff housing, wherein the elongated flexible band forms a loop with a first circumferential length when the cuff retainer is in a latched state, and the elongated flexible band forms a loop with a second circumferential length when in the unlatched state, the second circumferential length being greater than the first circumferential length, the cuff housing further including a top surface with at least one support rod attached to the top surface and projecting away from the cuff housing in a substantially perpendicular direction, and the cuff retainer is further comprised of a bottom surface with at least one linear bearing adapted to receive the at least one support rod, the at least one support rod and the at least one linear bearing forming a slidable connection permitting the cuff retainer to translate away from the cuff housing when the cuff retainer is in the unlatched state.

30. The apparatus of claim 29 wherein the cuff retainer is further comprised of a latching mechanism having an actuator connected to the latching mechanism and the cuff housing is further comprised of a receiver adapted to latchably engage the latching mechanism when the cuff retainer is in the latched position.

31. The apparatus of claim 30 wherein the latching mechanism is further comprised of a pawl, and the receiver is an aperture adapted to latchably engage the pawl.

32. The apparatus of claim 30 wherein the actuator is further comprised of a manual release knob accessible to the user.

33. The apparatus of claim 30 wherein the latching mechanism is further comprised of an electrically actuated solenoid.

34. The apparatus of claim 30 wherein the latching mechanism is further comprised of a pneumatically actuated air cylinder.

35. A pneumatic blood pressure cuff apparatus for blood pressure measurements, comprising:

an elongated flexible band of predetermined length adapted to be inflated, the length having a first and a second end;

a cuff housing attached to a first end of the elongated flexible band, the cuff housing further including a top surface; and a cuff retainer connected to the second end of the elongated flexible band, the cuff retainer being releasably latchable and slidably connected to the cuff housing, wherein the elongated flexible band forms a loop with a first circumferential length when the cuff retainer is in a latched state, and the elongated flexible band forms a loop with a second circumferential length when in the unlatched state, the second circumferential length being greater than the first circumferential length, and further wherein the cuff retainer and the cuff housing are slidably connected by at least one linear guide track adapted to permit translation of the cuff retainer relative to the cuff housing when the cuff retainer is in the unlatched state, the at least one linear guide track being attached to the top surface of the cuff housing.

36. The apparatus of claim 35 wherein the cuff retainer is further comprised of a latching mechanism having an actuator connected to the latching mechanism and the cuff housing is further comprised of a receiver adapted to latchably engage the latching mechanism when the cuff retainer is in the latched position.

37. The apparatus of claim 36 wherein the actuator is further comprised of a manual release knob accessible to the user.

38. The apparatus of claim 36 wherein the latching mechanism is further comprised of an electrically actuated solenoid.

39. The apparatus of claim 36 wherein the latching mechanism is further comprised of a pneumatically actuated air cylinder.

40. The apparatus of claim 36 wherein the latching mechanism is further comprised of a pawl, and the receiver is an aperture adapted to latchably engage the pawl.

41. A pneumatic blood pressure cuff apparatus for blood pressure measurements, comprising:

an elongated flexible band of predetermined length adapted to be inflated, the length having a first and a second end;

a cuff housing attached to a first end of the elongated flexible band, the cuff housing further including a front surface; and a cuff retainer connected to the second end of the elongated flexible band, the cuff retainer being releasably latchable and slidably connected to the cuff housing, wherein the elongated flexible band forms a loop with a first circumferential length when the cuff retainer is in a latched state, and the elongated flexible band forms a loop with a second circumferential length when in the unlatched state, the second circumferential length being greater than the first circumferential length, and further wherein the cuff retainer and the cuff housing are slidably connected by at least one linear guide track adapted to permit translation of the cuff retainer relative to the cuff housing when the cuff retainer is in the unlatched state, the at least one linear guide track being attached to the front surface of the cuff housing.

42. The apparatus of claim 41 wherein the cuff retainer is further comprised of a latching mechanism having an actuator connected to the latching mechanism and the cuff housing is further comprised of a receiver adapted to latchably engage the latching mechanism when the cuff retainer is in the latched position.

43. The apparatus of claim 42 wherein the actuator is further comprised of a manual release knob accessible to the user.

44. The apparatus of claim 42 wherein the latching mechanism is further comprised of an electrically actuated solenoid.

45. The apparatus of claim 42 wherein the latching mechanism is further comprised of a pneumatically actuated air cylinder.

46. The apparatus of claim 42 wherein the latching mechanism is further comprised of a pawl, and the receiver is an aperture adapted to latchably engage the pawl.

47. A pneumatic blood pressure cuff apparatus for blood pressure measurements, comprising:

an elongated flexible band of predetermined length adapted to be inflated, the length having a first and a second end;

a cuff housing attached to a first end of the elongated flexible band; and a cuff retainer connected to the second end of the elongated flexible band, the cuff retainer being releasably latchable to the cuff housing, wherein the elongated flexible band forms a loop with a first circumferential length when the cuff retainer is in a latched state, and the elongated flexible band forms a loop with a second circumferential length when in the unlatched state, the second circumferential length being greater than the first circumferential length, the cuff retainer further including a bottom surface with at least one support rod attached to the bottom surface and projecting away from the cuff retainer in a substantially perpendicular direction, and the cuff housing is further comprised of a top surface with at least one linear bearing adapted to receive the at least one support rod, the at least one support rod and the at least one linear bearing forming a slidable connection permitting the cuff retainer to translate away from the cuff housing when the cuff retainer is in the unlatched state.

48. The apparatus of claim 47 wherein the cuff retainer is further comprised of a latching mechanism having an actuator connected to the latching mechanism and the cuff housing is further comprised of a receiver adapted to latchably engage the latching mechanism when the cuff retainer is in the latched position.

49. The apparatus of claim 48 wherein the actuator is further comprised of a manual release knob accessible to the user.

50. The apparatus of claim 48 wherein the latching mechanism is further comprised of an electrically actuated solenoid.

51. The apparatus of claim 48 wherein the latching mechanism is further comprised of a pneumatically actuated air cylinder.

52. The apparatus of claim 48 wherein the latching mechanism is further comprised of a pawl, and the receiver is an aperture adapted to latchably engage the pawl.

* * * * *

UNITED STATES PATENT AND TRADEMARK OFFICE
CERTIFICATE OF CORRECTION

PATENT NO.   : 6,471,657 B2
DATED        : October 29, 2002
INVENTOR(S)  : Alireza Sadritabrizi It is certified that error appears in the above-identified patent and that said Letters Patent is hereby corrected as shown below:

Column 1,
Line 16, "heart attack, or a" should read -- heart attack or a --

Column 2,
Line 62, "tensioning devices" should read -- tensioning device --

Column 3,
Lines 43, 48 and 51, "view the embodiment" should read -- view of the embodiment --

Column 4,
Line 57, "When inner cuff" should read -- When the inner cuff --
Line 58, "within outer cuff" should read -- within the outer cuff --

Column 9,
Lines 55 and 66, "of claim 8 wherein" should read -- of claim 13 wherein --

Signed and Sealed this

Ninth Day of September, 2003

JAMES E. ROGAN
*Director of the United States Patent and Trademark Office*